(12) United States Patent
Torres et al.

(10) Patent No.: US 6,555,661 B1
(45) Date of Patent: Apr. 29, 2003

(54) SIMPLE, ENVIRONMENTALLY BENIGN, METHOD FOR PURIFYING PROTEIN A

(76) Inventors: Anthony R. Torres, 79 E. 2050 North, Centerville, Davis County, UT (US) 84014; Walter H. Runkis, 33 Turner Rd, Danbury, Fairfield County, CT (US) 06810

( * ) Notice: Subject to any disclaimer, the term of this patent is extended or adjusted under 35 U.S.C. 154(b) by 0 days.

(21) Appl. No.: 09/486,417

(22) PCT Filed: Aug. 25, 1998

(86) PCT No.: PCT/US98/17628

§ 371 (c)(1), (2), (4) Date: Feb. 25, 2000

(87) PCT Pub. No.: WO99/10370

PCT Pub. Date: Mar. 4, 1999

Related U.S. Application Data

(60) Provisional application No. 60/056,786, filed on Aug. 25, 1997.

(51) Int. Cl.⁷ .............................. C07K 1/14; C07K 1/18
(52) U.S. Cl. ..................... 530/517; 530/412; 530/416
(58) Field of Search ................... 530/412, 416, 530/417

(56) References Cited

U.S. PATENT DOCUMENTS

| | | | |
|---|---|---|---|
| 5,075,423 A | 12/1991 | Balint | 530/350 |
| 5,169,936 A | 12/1992 | Staples et al. | 530/350 |
| 5,648,237 A | 7/1997 | Carter | 435/69.1 |

OTHER PUBLICATIONS

Database Wpids on Stn, Derwent Information, Ltd. AN 86–302595. JP 61224997 A (Kagaku Oyobi Kessei Ryoho) Oct. 6, 1986.

*Primary Examiner*—Michael Borin

(57) ABSTRACT

High purity protein A is recovered from protein A preparations by passing a protein A preparation over an ion exchange column so that protein A will bind to a cation exchange resin. The loaded column is washed with a wash buffer solution having about the same pH as the protein A preparation and an increased mineral salt concentration to elute certain impurities but not the protein A. The protein A is eluted from the washed column by eluting the column with an elution buffer solution having a pH higher than the wash buffer solution and mineral salt concentration substantially no higher than the wash buffer solution. The protein A can be easily recovered from protein A preparations that do not use any human or animal components. The protein A purified by the invention is suitable for all common uses of protein A, but is especially well-suited for human therapeutic applications.

16 Claims, No Drawings

SIMPLE, ENVIRONMENTALLY BENIGN, METHOD FOR PURIFYING PROTEIN A

This application claims the benefit of Provisional Application No. 60/056,786, filed Aug. 25, 1997.

BACKGROUND OF THE INVENTION

1. Field

The invention relates to high-purity protein A recovery from preparations such as supernatants and cell lysates, more particularly, to a process for purification by contacting protein A with a suitable ion exchange material.

2. State of the Art

Several references describing the purification of protein A point the way to conventional purification strategies. One method (Balint, Jr,; U.S. Pat. No. 5,075,423; 1991) involves binding protein A to $I_gG$, or $I_gG$ fragments (preferably human $I_gG$), coupled to a suitable support on an anion exchange resin such as DEAE-cellulose. This affinity chromatography process must be followed by ion exchange chromatography to reduce the quantity of contaminants, such as HIV viral envelope antigens and $I_gG$ ligand that commonly leaches from the support and elute with the protein A. This process has two main disadvantages:

(i) Although ion exchange chromatography can significantly reduce the amount of antigens and other contaminants leached from the support, this step cannot entirely eliminate these contaminants, making the protein A purified by this process of questionable utility for therapeutic applications;

(ii) Since this process uses both affinity chromatography and ion exchange chromatography, it will tend to be uneconomical for the following reasons:

(a) affinity chromatography resins are expensive and have shorter usable lives than hydrophobic interaction chromatography (HIC) resins or ion exchange resins;

(b) affinity chromatography resins have lower binding capacities than HIC resins or ion exchange resins, requiring the use of larger size equipment, such as tanks, pumps, columns, etc.;

(c) the use of larger size equipment for affinity chromatography requires proportionally greater amounts of processing time, reagents consumed, and generates more waste products which must be discharged or otherwise disposed of;

(d) on a manufacturing scale, the two entirely different process steps referred to above (affinity and ion exchange) would require separate equipment for both process steps.

Another invention process (Love, et al. U.S. Pat. No. 5,314,993; 1994) provides a complicated, multistep method to purify protein A This process has greater utility for therapeutic applications of protein A than that of Balint, Jr., cited above, but is not cost-effective and has the additional disadvantages:

(i) This process requires the protein A preparation to be heated to a temperature of from 50° C. to 80° C. for 30 seconds which causes "some contaminating protein to precipitate". This procedure is an inefficient purification step since some protein A would certainly be lost by "trapping" and precipitate along with the other proteins thus precipitated. Moreover, using this step to purify protein A on a manufacturing scale (typically 100 liters to 1,000 liters, or more) will require additional capital expenditures for equipment and will consume large amounts of energy;

(ii) Some of the reagents used by the process are environmentally harmful and must be reclaimed or disposed of as hazardous waste.

Protein A is an antibody binding reagent which binds the FC portion of all human antibodies (except $I_gG_3$), and some types of antibodies from other animal species such as pig, dog, rabbit, goat, and mouse, among others. Protein A is a component of a wide range of biotechnology and biomedical applications. Protein A may be coupled to supports such as silica, agarose, cellulose, or cross-linked dextran to make affinity chromatography resins to purify antibodies, proteins, peptides, etc. Protein A may be coupled to support, such as agarose, for use as an immunoprecipitant to clarify antibodies from biological solutions. Protein A is commonly used as a component of testing methods, such as agglutination, ELISA, and Western blots, as well as many other well-known applications. Protein A is also used in a growing number of therapeutic applications to bind immunocomplexes and immunoglobulins from blood and serum (Terman, et al.).

Protein A has become so important to biotechnology and biomedicine that "Genetic Engineering News" on its Free Product Information card, includes it as one of the 30 categories of "Chemical—Biologicals" in which a scientist would be expected to be interested, along with "Organic Chemicals", "Fermentation Nutrients" and "Cell Culture Media".

The present invention provides a simple, cost-effective, environmentally benign method of producing high purity, high yield, protein A from a wide variety of protein A preparations. In its simplest embodiment it is essentially a one step process. Using the present invention, a high purity protein A can be obtained by loading a protein A preparation onto a cation exchange column, washing the column with a suitable buffer solution to remove impurities, and eluting the protein A fraction from the column as a single step elution.

Most well-known protein purification schemes, such as those reported in "Pharmacia Separation News" and elsewhere, call for a multistep approach to separate a protein of interest from its impurities. At each step, some impurities are eliminated as a result of properties those impurities share in common, which are not shared by the protein of interest. When the inventors began research aimed at discovering a novel method to purify protein A by means of ion exchange chromatography, they believed a multistep purification scheme was the correct approach. However, during the course of this research, peculiarities were observed regarding the behavior of protein A when bound to strong cation exchange resins, such as Fractogel EMD-$SO_3$, manufactured by EM Separations.

It was unexpectedly discovered that by exploiting certain characteristics inherent in some cation exchange resins, high purity protein A could be separated from a protein A-containing preparation in essentially a single step. The object of the invention process is achieved by carefully controlling the buffer conditions by which protein A, in a protein A-containing preparation, is loaded, washed and eluted. These conditions are not documented in prior art and are not obvious to someone skilled in the art of chromatography.

Protein A purified by the process invention can be economically recovered from many types of protein A-containing preparations with high yield and high purity. The simplicity provided by the present invention will reduce the production cost of protein A. Since protein A is the costliest component in most products produced using protein A, reducing the purification cost of protein A should generally benefit the biotechnology and biomedical industries.

The present invention is also more environmentally benign than existing processes. The invention process does not use any reagents which are environmentally harmful. Waste reagents do not need to be reclaimed, or otherwise disposed of as environmentally unsafe. Moreover, the present invention does not use any human- or animal-derived products or by-products, giving the process invention broad utility for human therapeutic applications.

SUMMARY OF THE INVENTION

The invention provides a process for the purification of protein A from a wide range of protein A-containing preparations. Purification of high purity protein A by the process invention is achieved:

(i) By removing cells and suspended solids from protein A preparations, such as cell culture supernatants and lysates, by centrifugation or hollow fiber filtration. The source of the protein A may be an extracellular protein A secreted by a natural or recombinant host organism, or from lysates produced to free protein A bond to the cell membranes of various strain of *Staphylococcus aureus,* or produced intracellularly in recombinant expression organisms, such as *Escherichia coli* or *Bacillus subtilis;*

(ii) Optionally, by using a "Bid Bead" chromatography resin or fluidized bed technique, cells and suspended solids may not need to be removed from a protein A preparation prior to adsorption;

(iii) Optionally, adsorption on an ion exchange column may be preceded by contacting a protein A preparation with an HIC resin, such as phenyl-HIC, then washing the column with about 100 to 300 mM acetate or citrate buffer, and eluting with distilled or deionized water. (This step is only desirable to save processing time when the salt concentration of a protein A preparation is too high for dilution with distilled or deionized water to be a practical consideration.);

(iv) By adsorbing protein A from a protein A preparation on a suitable cation exchange resin followed by washing and selective elution of the protein A fraction. (This does not generally require ultrafiltration and desalting that is often necessary when adsorption is done on other resins. Instead, preparations can be diluted with distilled or deionized water to a conductivity level that will allow absorption, usually from 1:2 to 1:4, v/v sample to water);

(v) For human therapeutic applications, and other applications where "ultra-pure" protein A is required, the eluent of several separations (about 3 to 5), described in paragraph "iv" above, may be pooled and diluted to about 13 mS with distilled or deionized water. A second separation as described in paragraph "iv" above may then be performed with selective elution of protein A. This separation is done on the same cation exchange column and in the same manner as the separation referred to in paragraph "iv".

The process invention would not be obvious to someone skilled in the art and provides various advantages over prior art, including certain unexpected advantages compared to the prior art processes. In addition to the advantages provided by the present invention, another advantage is that the process invention does not resort to the use of human or animal components and/or by-products to obtain high purity protein A, making it particularly suitable for the production of human therapeutic products.

Prior art commonly uses $I_gG$ affinity resins as an initial capture step to remove protein A from bacterial preparations. In such processes, contamination of the protein A eluent from leached $I_gG$ molecules and fragments is unavoidable. Moreover, other human- or animal-derived contaminants may also leach from affinity resins, such as viral antigens that were present with the $I_gG$ when it was coupled to the support. These contaminants are reduced by subsequent ion exchange chromatography on an anion exchange resin such as DEAE. Although every precaution is presumably taken to insure that such contaminants are removed during additional downstream processing, not using human- and animal-derived components anywhere in the process offers the greatest probability of producing a contaminant-free product. This is especially important for applications where protein A is used for human therapeutic purposes, such as that described by Bensinger in U.S. Pat. No. 4,614,513; 1986.

An unexpected advantage of the invention process is obtained by means of exploiting certain functional characteristic of cation exchange resins. By so doing, a reduction of processing time, and the amount of reagent needed to purify protein A, is achieved. For many applications, protein A can be suitably separated from a protein A preparation by merely diluting said preparation, adjusting the pH, and eluting the protein A as a substantially pure product. For applications where ultrahigh purity is desired, the eluent-containing protein A fractions from 3 to 6 separations can be pooled and separated a second time using the same chromatography equipment, ion exchange resin, and process as the previous ion exchange separation, except the reagent used during the wash step is reduced to one-fourth that used during the initial separation. This aspect makes the present invention considerably simpler and potentially more economical than prior art.

DETAILED DESCRIPTION OF THE PREFERRED EMBODIMENT

In its simplest embodiment the present invention uses only a single ion exchange chromatography separation on a cation exchange resin. Cation exchange resins from three manufacturers have been tried with varying results. By exploiting certain properties of this type of resin, the need for additional chromatographic separations is generally not necessary, although some hydrophobic interaction (HIC) resins, such as Phenyl-HIC, may be employed as an initial capture step to economically pretreat preparations which have dissolved salt concentrations too high for dilution in distilled or deionized water alone to be economically practical.

(1) After a bacterial culture is grown to optimal density, it may be stabilized by the addition of protease inhibitors and subjected to centrifugation or hollow fiber filtration to remove insoluble components. A desalting step may also be done prior to chromatography, but is generally unnecessary.

(2) In the present invention, a clarified protein A-containing preparation may be undiluted or diluted. If said protein A preparation has a conductivity of about 30 to 35 mS, the preparation may be diluted up to 300% or more with deionized or distilled water, and its pH lowered to about 3.0 to 5.5 with acetic acid or citrate acid (preferably acetic acid), resulting in a preparation with a pH of about 4.5 and a conductivity of about 13 mS.

(3) Optionally, if the conductivity of the undiluted protein A-containing preparation is substantially above 30 ms, the protein A-containing preparation may be loaded onto a column containing an HIC resin (such as Phenyl HIC). The HIC column is then washed with a wash buffer solution comprising about 10 to 50 mM acetate or citrate buffer and about 75 to 125 mM sodium chloride or potassium chloride (preferably 10 mM acetate buffer containing 2100 mM sodium chloride, having a pH of about 4.5) The wash buffer solution may also contain protease inhibitors, such as EDTA and soybean trypsin inhibitor. After washing, the HIC column is then eluted with distilled or deionized water. This step serves as a desalting step. It also removes some impurities resulting in increased column capacity during the cation exchange step which follows. The present step is recommended only as a pretreatment for protein A preparations which are too high in dissolved salts or proteinaceous impurities to make dilution alone of the protein A-containing preparation a suitable preparatory procedure for ion exchange chromatography.

(4) If the conductivity of the protein A-containing preparation is substantially below 13 mS, sodium chloride or potassium chloride (preferably sodium chloride) should be added to the preparation to increase the conductivity thereof to about 11 to 13 mS. If the salt concentration of the protein A-containing preparation is substantially below 13 mS, additional proteinaceous impurities may bind the ion exchange resin and reduce the resin's capacity to bind protein A. Furthermore, such impurities may elute with the protein A, thereby resulting in an unsatisfactory separation.

(5) A chromatography column packed with a cation exchange resin (such as Fractogel EMD-$SO_3$) is equilibrated using an equilibration buffer solution comprising about 10 to 50 mM acetate or citrate buffer containing about 110 mM to 130 mM sodium chloride or potassium chloride. Said equilibration buffer solution should be formulated to approximate the conductivity and pH of the protein A-containing preparation to be loaded (preferably 50 mM acetate buffer, containing about 121 mM sodium chloride, having a pH of about 4.5 and conductivity of about 13 mS). Under these conditions protein A will bind to the cation exchange resin, but most impurities will flow through.

(6) Next the column is washed with a wash buffer solution comprising about 10 to 50 mM acetate or citrate buffer containing about 200 to 350 mM sodium chloride or potassium chloride. Said wash buffer solution should have a pH about the same as that of the equilibration buffer solution (preferably 50 mM acetate buffer containing 275 mM sodium chloride, having a pH of about 4.5 and conductivity of about 29 mS). This step removes impurities that elute very close to the elution conditions of protein A. The column is washed until a low UV 280 mm reading is obtained (usually about 10 to 12 column volumes of wash buffer solution are required). The wash buffer solution may also contain protease inhibitors, such as EDTA and soybean trypsin inhibitor. A nonionic detergent, such as CHAPS, CHAPSO, Triton X-100, or Triton XL-80N may also be added to the above or used as a separate "finishing" wash step.

(7) The column is then eluted with an equilibration buffer solution comprising about 10 to 50 mM acetate buffer or citrate buffer containing about 200 to 350 mM sodium chloride or potassium chloride, having a pH slightly higher than the wash buffer solution (preferably 50 mM acetate buffer containing about 250 mM sodium chloride, having a pH of about 4.7 and conductivity of about 27 mS). By raising the pH very slightly, and leaving the salt concentration at the same level or at a slightly lower level than the wash buffer solution, the protein A fraction step elutes as a substantially pure product.

(8) Optionally, for applications of protein A where ultra-purity is desirable, such as human therapeutic uses, the eluent collected from up to 5 separations, as described in paragraph 7 above, may be pooled. An additional separation process may then be performed in the manner described in paragraphs 5 through 7 above, except that the volume of wash buffer solution used to wash the column, as described in paragraph 6 is reduced to 4 column volumes.

Although the description above contains many specificities, these should not be construed as limiting the scope of the invention, but as merely providing illustrations of some of the presently preferred embodiments thereof. For example, the invention process could be used to purify enzymes, peptides, and proteins other than protein A, such as protein G, and Steptavidin, among others.

The international market for protein A has been estimated at over $100 million annually. Every year, additional papers announcing new uses and applications of protein A appear in scientific journals. Protein A is now used in numerous products and its popularity is expected to continue increasing into the foreseeable future. The simple elegance of the present invention process promises to benefit mankind by providing the biotechnology and biomedical industries with protein A that is of the highest purity at the lowest possible cost. Price reductions in products containing protein A purified by the present invention could range from 20% to 50% below present market levels. Since the invention uses no human or animal products, it is expected to have broad utility in human therapeutic applications.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

We claim:

1. A process for the purification of protein A from a protein A preparation which comprises:
   (a) loading an ion exchange column by passing said protein A preparation with a pH of about 4.5 over said column under conditions of mineral salt concentration so that the protein A will bind to a cation exchange resin;
   (b) washing the loaded column with a wash buffer solution having a pH of about 4.5 and increased mineral salt concentration high enough to elute certain impurities but not high enough to elute the protein A bound to the cation exchange resin; and
   (c) eluting the column with an elution buffer solution having a pH of about 4.7 and mineral salt concentration no higher than the wash buffer solution to elute the protein A as a substantially pure solution, but not substantially elute remaining impurities bound to the cation exchange resin.

2. A process of claim 1 wherein said protein A preparation is derived from *Staphylococcus aureus*.

3. A process of claim 1 wherein said protein A preparation is derived from a host organism, such as *Escherichia coli* or *Bacillus subtilis*, containing a gene encoded to express recombinant protein A.

4. A process of claim 1 wherein said protein A preparation is pretreated by loading the protein A preparation onto a hydrophobic interaction chromatography (HIC) column.

5. A process of claim 4 wherein the HIC column is washed with a wash buffer solution having a pH of about 3.0 to 4.5.

6. A process of claim 5 wherein said wash buffer solution comprises about 10 mM acetate or citrate buffer and about 50 to 100 mM sodium chloride or potassium chloride.

7. A process of claim 6 wherein said wash buffer solution also contains about 1 to 5 mM ethylenediaminetetraacetic acid (EDTA) and about 2 to 5 mM soybean trypsin inhibitor.

8. A process of claim 4 wherein the HIC column is eluted with distilled or deionized water, whereby a partially purified protein A preparation is eluted having substantially reduced concentration of salts and some reduction of proteinaceous contaminants.

9. A process of claim 1 wherein said buffer solution comprises about 10 to 50 mM acetate or citrate buffer and about 250 to 300 mM sodium chloride or potassium chloride.

10. A process of claim 9 wherein said wash buffer solution contains about 1 to 5 mM EDTA and about 2 to 5 mM soybean trypsin inhibitor.

11. A process of claim 9 wherein said wash buffer solution contains a zwitterionic or nonionic detergent, such as CHAPS, CHAPSO, Triton X-100, or Triton XL-80N.

12. A process of claim 1 wherein the cation exchange column is eluted with an elution buffer solution having a pH of about 4.6 to 4.9, whereby a substantially purified protein A preparation is eluted.

13. A process of claim 12 wherein said elution buffer solution comprises about 10 to 50 mM acetate or citrate buffer and about 250 to 300 mM sodium chloride or potassium chloride.

14. A process according to claim 1, wherein the protein A preparation has a pH of about 4.5 and a salt concentration of about 121 mM.

15. A process according to claim 14, wherein the wash buffer solution has a salt content between about 200 mM and 350 mM.

16. A process according to claim 15 wherein the salt content of the wash buffer solution is about 275 mM.

* * * * *